United States Patent

Watanabe et al.

[11] Patent Number: 4,723,044
[45] Date of Patent: Feb. 2, 1988

[54] PRODUCTION OF DIBROMONITRO COMPOUND

[75] Inventors: Michio Watanabe, Yamato; Kiyoshi Ishii, Yokohama; Mie Namiki, Hiratsuka; Takeshi Fukuda, Yokohama, all of Japan

[73] Assignee: Permachem Asia, Ltd., Tokyo, Japan

[21] Appl. No.: 874,144

[22] Filed: Jun. 13, 1986

[30] Foreign Application Priority Data

Jun. 17, 1985 [JP] Japan .................. 60-130032

[51] Int. Cl.$^4$ .............................. C07C 79/18
[52] U.S. Cl. ..................... 568/713; 568/712
[58] Field of Search ........... 568/712, 713, 711, 709

[56] References Cited

U.S. PATENT DOCUMENTS

| 2,164,440 | 7/1939 | Wyler | 568/712 |
| 2,231,403 | 2/1941 | Wyler | 568/712 |
| 3,564,062 | 2/1971 | Tindall | 568/712 |
| 3,658,921 | 4/1972 | Wessendorf | 568/712 |
| 3,711,561 | 1/1973 | Wessendorf | 568/712 |

FOREIGN PATENT DOCUMENTS

| 0137276 | 4/1985 | European Pat. Off. | 568/712 |
| 1954173 | 5/1971 | Fed. Rep. of Germany | 568/71 |
| 0072108 | 9/1973 | Japan | 568/713 |
| 0003011 | 1/1977 | Japan | 568/713 |
| 0002242 | 1/1982 | Japan | 568/713 |

OTHER PUBLICATIONS

Journal of Chemical Society, Perkin II, 1107–1110 (1973).
Journal of Medicinal Chemistry, vol. 17, No. 9, 977–981 (1974).

Primary Examiner—Werren B. Lone
Attorney, Agent, or Firm—Sherman and Shalloway

[57] ABSTRACT

A process for producing a dibromonitro compound represented by the general formula

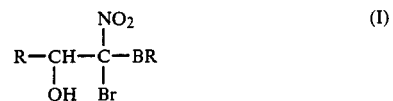

wherein R represents a hydrogen atom or a methyl group, which comprises condensing nitromethane with formaldehyde or acetaldehyde in the presence of an alkali, the amount of the aldehyde being at least 1.5 moles per mole of nitromethane; and thereafter without isolating the product, treating the reaction mixture with bromine to brominate the product.

3 Claims, No Drawings

PRODUCTION OF DIBROMONITRO COMPOUND

This invention relates to a novel process for producing a dibromonitro compound expressed by general formula

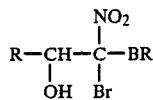

wherein R represents a hydrogen atom or a methyl group.

Brominated nitro compounds are known to have strong fungicidal activity and used as therapeutic and industrial fungicides.

For the production of the compound of formula (I), there have been known, for example, a method which comprises suspending a sodium salt of 2-bromo-2-nitroethanol in cold diethyl ether, adding a chloroform solution of bromine to the suspension, and performing the reaction (see Chemische Berichte 56B, 618, 1923), a method which comprises reacting 2-bromo-2-nitropropanediol-1,3 with potassium hypobromite (see Chemische Berichte 57B, 2127–2128), and a method of reacting 2-nitroethanol with bromine in the presence of $OH^-$ (see Journal of Chemical Society 1973 (8), 1107). These methods, however, have the defect that the yield is low, and because of the explosive nature of the salt of the nitro compound, the operation may involve danger.

It is an object of this invention to provide a process for producing the compound of formula (I) in a high purity and a high yield.

According to this invention, there is provided a process for producing a dibromonitro compound represented by the general formula

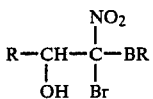

wherein R represents a hydrogen atom or a methyl group,
which comprises condensing nitromethane with formaldehyde or acetaldehyde in the presence of an alkali, the amount of the aldehyde being at least 1.5 moles per mole of nitromethane; and thereafter without isolating the product, treating the reaction mixture with bromine to brominate the product.

The process of this invention enables the desired product of high purity to be obtained in an unexpectedly high yield.

Formaldehyde or acetaldehyde can be used as such or as a solution in a solvent such as water. Paraformaldehyde may be used as the formaldehyde. The amount of the aldehyde is at least 1.5 moles, preferably 1.5 to 2.5 moles, especially preferably 2 moles, per mole of nitromethane. If its amount is smaller than the lower limit, the compound of formula (I) cannot be obtained in a high yield.

Examples of the alkali used are sodium hydroxide, potassium hydroxide, barium hydroxide, calcium hydroxide, sodium carbonate, sodium hydrogen carbonate, sodium methoxide, sodium ethoxide, potassium methoxide, and potassium ethoxide. The amount of the alkali used is preferably nearly two times the equivalent weight of nitromethane, but may exceed it.

In the practice of the present invention, 1 mole of nitromethane and at least 1.5 moles of formaldehyde or acetaldehyde are, for example, dissolved in a solvent, and after adding the alkali, condensed.

Examples of the solvent are water, lower alcohols, glycols, acetic acid dimethylformamide, dioxane, toluene, octane, and halogen compounds. The condensation reaction temperature is −20° C. to +20° C., preferably −5° C. to 0° C.

After the condensation reaction, bromine is added to the reaction mixture without isolating the product, and reacted with the product. Bromine may be added as such, or it is also possible to dissolve it in a solvent such as methanol, acetic acid or dichloromethane and add the solution dropwise. The amount of bromine is generally nearly two times the equivalent weight of nitromethane or larger, and may be nearly equivalent to the amount of the alkali. The bromination reaction temperature is −20° C. to +30° C., preferably −10° C. to +15° C.

After the reaction, the reaction mixture is left to stand into an upper layer and a lower layer, and the oily product as the lower layer is collected. As required, the oily product is distilled under reduced pressure to give the dibromonitro compound of high purity.

The dibromonitro compound of formula (I) obtained by the process of this invention can be used as a therapeutical or industrial fungicide. It is particularly useful as a controlling agent for slime occurring in the paper-making process due to mircroorganisms in water.

The following examples illustrate the present invention in greater detail.

EXAMPLE 1

A four-necked flask equipped with a condenser tube, a thermometer and a stirrer was charged with 61.0 g (1.0 mole) of nitromethane, 150 g of water and 162.2 g (2.0 moles) of a 37% aqueous solution of formaldehyde. With stirring, the mixture was cooled, and a solution of 80 g (2.0 moles) of sodium hydroxide in 240 g of water was slowly added dropwise while it was kept at −5° to 0° C. The reaction solution gradually became turbid whitely. After the addition, the solution was stirred for 1 hour, and then 319.6 g (2.0 moles) of bromine was added dropwise at 0° to 5° C. After the addition, the reaction solution was transferred to a separation funnel and left to stand, whereupon it separated into two layers. The oily product as the lower layer was collected. When part of the oily product was distilled, a distillate having a boiling point of at 85° C./2 mmHg was obtained. The distillate was left to stand to give 2,2-dibromo-2-nitroethanol as a pure white solid having a melting point of 30° C. Elemental analysis of this compound gave the following results.

|  | C | H | N | Br |
|---|---|---|---|---|
| Found (%): | 9.88 | 1.41 | 5.50 | 65.5 |
| Calculated (%): | 9.65 | 1.22 | 5.63 | 64.2 |

The above procedure was repeated except that the amount of formaldehyde was changed as indicated in Table 1.

The results are shown in Table 1.

The content of 2,2-dibromo-2-nitroethanol in the oily product was determined by a liquid chromatographic method, and the yield of 2,2-dibromo-2-nitroethanol is the percentage against theory based on nitromethane.

TABLE 1

| | Amounts of the starting materials moles | | Oily product | 2,2-Dibromo-2-nitroethanol | |
|---|---|---|---|---|---|
| | Nitromethane | Formaldehyde | Amount (g) | Content in the oily product (%) | Yield (%) |
| Invention | 1 | 1.5 | 190 | 81.0 | 61.8 |
| | 1 | 2.0 | 212 | 86.1 | 73.3 |
| | 1 | 2.5 | 194 | 84.2 | 65.6 |
| Comparison | 1 | 1.0 | 148 | 42.5 | 25.2 |
| | 1 | 1.2 | 133 | 47.4 | 25.3 |

EXAMPLE 2

A four-necked flask equipped with a condenser tube, a thermometer and a stirrer was charged with 6.1 g (0.1 mole) of nitromethane, 15 g of water and 16.2 g (0.2 mole) of a 37% aqueous solution of formaldehyde. The mixture was cooled, and a solution of 10.6 g (0.1 mole) of sodium carbonate in 150 ml of water was slowly added dropwise while it was kept at 0° to 5° C. After the addition, the solution was stirred for 1 hour, and then 32.0 g (0.2 mole) of bromine was added dropwise to 5° to 10° C. After the addition, the reaction solution was transferred to a separating funnel and left to stand, whereupon it separated into two layers. The oily product as the lower layer was obtained in an amount of 20.6 g. The content of 2,2-dibromo-2-nitroethanol in the oily product was 86.4%, and the yield of this compound was 71.5%.

EXAMPLE 3

A four-necked flask equipped with a condenser tube, a thermometer and a stirrer was charged with 6.1 g (0.1 mole) of nitromethane, 15 ml of methanol and 16.2 g (0.2 mole) of a 37% aqueous solution of formaldehyde. With stirring, the mixture was cooled, and a solution of 10.8 g (0.2 mole) of sodium methoxide in 30 ml of methanol was slowly added dropwise while it was kept at −5° to 0° C. After the addition, the solution was stirred for 1 hour, and 32.0 g (0.2 mole) of bromine was added dropwise at 0° to 5° C. After the addition, the solution was stirred at the same temperature for 1 hour, and water and methanol were removed by a rotary evaporator. The residue was transferred to a separating funnel, and after addition of water, shaken to remove sodium bromide. The oily product was obtained in an amount of 19.7 g. The content of 2,2-dibromo-2-nitroethanol in the oily product was 85.3% and the yield of this compound was 67.5%.

EXAMPLE 4

A four-necked flask equipped with a condenser tube, a thermometer and a stirrer was charged with 6.1 g (0.1 mole) of nitromethane, 15 g of water and 13.8 g (0.17 mole) of a 37% aqueous solution of formaldehyde. With stirring, the mixture was cooled, and a suspension of 7.4 g (0.1 mole) of calcium hydroxide in 40 ml of water was added dropwise at 0° to 10° C. After the addition, the mixture was stirred for 1 hour, and 32.0 g (0.2 mole) of bromine was added at −10° to 0° C. After the addition, the reaction mixture was transferred to a separating funnel and left to stand. The oily product (lower layer) was obtained in an amount of 18.9 g. The content of 2,2-dibromo-2-nitro-ethanol in the oily product was 62.4%, and the yield of this compound was 62.6%.

EXAMPLE 5

A four-necked flask equipped with a condenser tube, a thermometer and a stirrer was charged with 61.0 g (1.0 mole) of nitromethane, 150 g of water and 110.3 g (2.0 moles) of an 80% aqueous solution of acetaldehyde. The mixture was cooled with stirring, and a solution of 80 g (2.0 moles) of sodium hydroxide in 240 g of water was slowly added dropwise at −10° to 0° C. After the addition, the solution was stirred for 1 hour, and 319.6 g (2.0 moles) of bromine was added dropwise at −5° to +5° C. After the addition, the reaction solution was transferred to a separating funnel and left to stand. The oily product (lower layer) was separated. Distillation of part of the oily product gave pure 1,1-dibromo-1-nitropropanol-2 as a pale yellow liquid having a boiling point of 75° C./1 mmHg. The elemental analysis of this compound gave the following results.

| | C | H | N | Br |
|---|---|---|---|---|
| Found (%): | 13.84 | 2.01 | 5.08 | 59.74 |
| Calculated (%): | 13.70 | 1.94 | 5.32 | 60.79 |

The above procedure was repeated except that the amount of acetaldehyde was changed as indicated in Table 2.

The results are shown in Table 2.

The yield of 1,1-dibromo-1-nitropropanol-2, and its content in the oily product were determined as in Example 1.

TABLE 2

| | Amounts of the starting materials (moles) | | Oily product | 1,1-Dibromo-1-nitropropanol-2 | |
|---|---|---|---|---|---|
| | Nitromethane | Acetaldehyde | Amount (g) | Content in the oily product (%) | Yield (%) |
| Invention | 1 | 1.5 | 198.6 | 80.8 | 61.0 |
| | 1 | 2.0 | 218.2 | 85.0 | 70.5 |
| | 1 | 2.5 | 215.6 | 81.3 | 66.7 |
| Comparison | 1 | 1.0 | 84.1 | 46.3 | 14.8 |
| | 1 | 1.2 | 110.4 | 42.4 | 17.8 |

EXAMPLE 6

A four-necked flask equipped with a condenser tube, a thermometer and a stirrer was charged with 6.1 g (0.1 mole) of nitromethane, 15 g of water and 11.0 g (0.2 mole) of an 80% aqueous solution of acetaldehyde. The mixture was cooled with stirring, and a solution of 11.2 g (0.2 mole) of potassium hydroxide in 30 g of water was slowly added dropwise at −5° to 0° C. After the addition, the solution was stirred for 1 hour, and 32 g (0.2 mole) of bromine was added dropwise at −5° to 0° C. After the addition, the reaction solution was transferred to a separating funnel, and left to stand. The oily product (lower layer) was obtained in an amount of 22.1 g. The content of 1,1-dibromo-1-nitro-propanol-2 in the oily product was 87.2%, and the yield of this compound was 73.3%.

EXAMPLE 7

Ethanol (50 ml) was put into a four-necked flask equipped with a condenser tube, a thermometer and a stirrer, and cooled to a temperature below 0° C. Then, 8.8 g, (0.2 mole) of acetaldehyde generated from paraformaldehyde and sulfuric acid was added. Then, 6.1 g (0.1 mole) of nitromethane was added, and with stirring, the mixture was cooled. A solution of 13.6 g (0.2 mole) of sodium ethoxide in 40 ml of ethanol was added dropwise while it was kept at −5° to 0° C. After the addition, the solution was stirred for 1 hour, and 32 g (0.2 mole) of bromine was added dropwise at −5° to 0° C. After the addition, the mixture was stirred at the same temperature for 1 hour, and ethanol was removed by a rotary evaporator. The residue was transferred to a separating funnel, and after addition of water, shaken to remove sodium bromide. The oily product (lower layer) was obtained in an amount of 21.3 g. The content of 1,1-dibromo-1-nitro-propanol-2 in the oily product was 89.7%, and the yield of this compound was 72.7%.

What is claimed is:

1. A process for producing a dibromonitro compound represented by the general formula

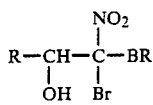

wherein R represents a hydrogen atom or a methyl group,
which comprises condensing nitromethane with formaldehyde or acetaldehyde in the presence of an alkali, the amount of the aldehyde being at least 1.5 moles per mole of nitromethane and the amount of alkali being at least two times the equivalent weight of nitromethane; and thereafter without isolating the product, treating the reaction mixture with bromine to brominate the product wherein the amount of bromine is two moles or more per mole of nitromethane.

2. The process of claim 1 wherein the amount of the aldehyde is 1.5 to 2.5 moles per mole of nitromethane.

3. The process of claim 1 wherein the alkali is selected from the group consisting of sodium hydroxide, potassium hydroxide, barium hydroxide, calcium hydroxide, sodium carbonate, sodium hydrogen carbonate, sodium methoxide, sodium ethoxide, potassium methoxide and potassium ethoxide.

* * * * *